United States Patent [19]

Buck et al.

[11] Patent Number: 4,673,766

[45] Date of Patent: Jun. 16, 1987

[54] METHOD OF PRODUCING BENZALDEHYDE

[75] Inventors: Keith T. Buck; Anthony J. Boeing; Joseph E. Dolfini, all of Cincinnati, Ohio

[73] Assignee: Mallinckrodt, Inc., St. Louis, Mo.

[21] Appl. No.: 856,595

[22] Filed: Apr. 25, 1986

[51] Int. Cl.$^4$ .............................................. C07C 45/51
[52] U.S. Cl. ...................................... 568/433; 568/458
[58] Field of Search ................................ 568/433, 458

[56] References Cited

PUBLICATIONS

Guthrie et al., Can. Jour. Chem., vol. 62 (1984), 1441–1445.

*Primary Examiner*—Bernard Helfin
*Attorney, Agent, or Firm*—Wood, Herron & Evans

[57] ABSTRACT

A method is disclosed for producing benzaldehyde by fractionally steam distilling benzaldehyde from cinnamaldehyde in the presence of hydroxide catalyst and at a pH on the order of about 11 to about 13. Conversions of cinnamaldehyde to benzaldehyde can be achieved on the order of about 75% or more.

8 Claims, No Drawings

METHOD OF PRODUCING BENZALDEHYDE

BACKGROUND OF THE INVENTION

The retroaldol reaction of cinnamaldehyde is well known. In this reaction, cinnamaldehyde is converted to benzaldehyde and acetaldehyde with various potential side reactions. Recently, for example, an investigation of the kinetics of the retroaldol reaction of cinnamaldehyde has been reported by J. Peter Guthrie, et al, *Can. J. Chem.*, Vol. 62, pp. 1441–1445 (1984). While the conversion of the cinnamaldehyde to benzaldehyde has been long known and well studied, it has not been heretofore known to produce benzaldehyde from cinnamaldehyde in substantial yields and favorable reaction conditions for production of such yields have not been reported.

SUMMARY OF THE INVENTION

This invention is directed to a method of making benzaldehyde by conversion of cinnamaldehyde in the presence of water with surprisingly high yields heretofore unachieved. The invention involves the dispersion of cinnamaldehyde in water and, in the presence of an effective catalytic amount of hydroxide ion, fractionally steam distilling benzaldehyde from the cinnamaldehyde. The reaction is conducted at a pH on the order of about 11 to about 13 and, unexpectedly, within this pH range it has been discovered that a substantial conversion of cinnamaldehyde to benzaldehyde can be achieved on the order of about 75% or more. It has also been found that the conversion may be achieved at such a high pH without adverse side reactions.

In a preferred mode of conducting the method, the cinnamaldehyde is dispersed in the water in the presence of shearing agitation and a surfactant. In another aspect of this invention, it is preferred to employ an anionic surfactant such as sodium lauryl sulfate. Preferably, the hydroxide ion is furnished by means of sodium hydroxide which also achieves the pH in the range of about 11 to about 13. It has critically been determined that the fractional steam distillation of benzaldehyde from the cinnamaldehyde must be conducted at a pH within the range of about 11 to about 13, preferably about 12 to about 12.5. Below and above this pH range, very poor conversions are obtained of 50% or far less and competing reactions interfere with the production of benzaldehyde. Outside of this critical pH range, side reactions, polymerization and other adverse reactions prohibit any significant yield of benzaldehyde. Yet, within the pH range of about 11 to about 13, especially about 12 to about 12.5, significant yields on the order of 75% or greater are achieved and benzaldehyde is recoverable in substantially pure form free of side reaction products. These results are considered to be unexpected especially at the high pHs of the reaction where it may have been expected that side reactions would have significantly lessened or prevented the yield for the desired product.

During the course of the fractional steam distillation of benzaldehyde from the cinnamaldehyde, acetaldehyde is also vaporized and removed. The removal of acetaldehyde thus prevents the forward polymerization reaction which otherwise competes in the presence of the catalyst. The benzaldehyde which has been steam distilled is then subsequently fractionally distilled for separation of the benzaldehyde from other components in the distillate such as minor amounts of acetaldehyde, terpenes and orthomethoxybenzaldehyde. It has also been found that a natural source for the cinnamaldehyde such as cassia oil may be employed containing a substantial amount of the natural cinnamaldehyde. Thus, a natural product such as cassia oil may be employed in the fractional steam distillation method of this invention and still the significant yields on the order of about 75% or more are achieved.

DETAILED DESCRIPTION

The following detailed operating example illustrates the practice of the invention in its most preferred form, thereby enabling a person of ordinary skill in the art to practice the invention. The principles of this invention, its operating parameters and other obvious modifications thereof will be understood in view of the following detailed procedure.

OPERATING EXAMPLE

A solution was made up from 38.6 lbs. sodium hydroxide, 4 lbs. sodium lauryl sulfate and 10 liters antifoam agent in 760 gallons of water. The solution was stirred until a homogeneous solution was obtained. Then, 1320 lbs. of cassia oil were placed in a 1150 gallon still. The oil contained approximately 72% by weight of cinnamaldehyde. The still had a pot volume of about 1150 gallons onto which was mounted a 4 foot fractionating column containing 1"×1" ceramic tubes and a water cooled condenser was thereafter connected in series for condensing the benzaldehyde-water azeotrope.

The above prepared sodium hydroxide solution was then added to the cassia oil and introduced into the pot of the still. The pot was equipped with a stirrer. Using pressurized steam and vigorous stirring, the pot was heated to reflux with a pot temperature of 105° C. Reflux was established with a column head temperature of about 99° C. Once reflux was established, it was continued for about 1 hour. During the course of the conversion of the cinnamaldehyde in the cassia oil to benzaldehyde, pH was monitored and was maintained at about 12 to about 12.5. In the event the pH fell below about 12, sodium hydroxide was added to bring the pH back up to the range of about 12–12.5. After refluxing for about 1 hour, take-off of the water-benzaldehyde azeotrope was initiated. The water cooled condenser was operated at 100° F. thereby enabling the water-benzaldehyde azeotrope to be condensed and collected in a chilled receiver. The acetaldehyde by-product was principally vaporized at the temperature of the condenser and was taken off as vapor. The distillate principally containing benzaldehyde in an amount of about 75% or more with minor amounts of cinnamaldehyde, terpenes, orthomethoxybenzaldehyde and acetaldehyde was obtained. The crude benzaldehyde was thus collected in a chilled receiver and, in a continuous feed operation the condensed water was continuously fed back to the still to replace what had been taken off and the distillation of the azeotrope continued. The fractional steam distillation of the crude benzaldehyde continued until about 670 lbs. of crude benzaldehyde were obtained. The crude distillate containing benzaldehyde was then dried under vacuum and fractionally distilled under vacuum of about 29" thereby providing a boiling point for the benzaldehyde at about 70° C. in order to obtain a substantially pure benzaldehyde free from residual terpenes and other impurities.

Thus, by means of practicing the above process, the objectives of this invention are achieved in that cinnamaldehyde is converted into benzaldehyde in substantially pure form even from the natural source of cassia oil. Surprisingly, it has been found that substantial yields in excess of 75% or more of substantially pure benzaldehyde are achieved by this method. Moreover, it has been found that there is a surprising window of high pH at which the conversion may take place in a fractional steam distillation column in order to separate the benzaldehyde and acetaldehyde from the reaction mixture and still avoid the adverse side reactions from occurring.

Having described this invention and its operating parameters, variations may be achieved without departing from the spirit and scope hereof.

What is claimed is:

1. A method of making benzaldehyde com- prising
   dispersing cinnamaldehyde in water,
   converting the cinnamaldehyde to benzaldehyde under the action of heat in the presence of a catalytic amount of hydroxide ion and at a pH of about 11 to about 13,
   fractionally steam distilling benzaldehyde and acetaldehyde from the cinnamaldehyde, and
   recovering benzaldehyde from the distillate.

2. The method of claim 1 which is conducted at a pH in the range of about 12 to about 12.5.

3. The method of claim 1 wherein the benzaldehyde distillate resulting from the steam distillation is fractionally distilled for separation of the benzaldehyde in substantially pure form.

4. The method of claim 1 wherein the acetaldehyde is vaporized during the course of the conversion while the benzaldehyde is condensed.

5. The method of claim 1 conducted in the presence of an anionic surfactant.

6. The method of claim 1 conducted under shearing agitation to facilitate the dispersion of the cinnamaldehyde in the water.

7. A method of making benzaldehyde com- prising
   dispersing cinnamaldehyde in water in the presence of an anionic surfactant,
   agitating the dispersion under the action of heat in the presence of a catalytic amount of hydroxide ion and at a pH of about 12 to about 12.5 for the conversion of cinnamaldehyde to benzaldehyde,
   fractionally steam distilling benzaldehyde and acetaldehyde from the cinnamaldehyde in a still having a pot temperature of about 105° C. and a column temperature of about 99° C., and
   fractionally distilling the benzaldehyde from the distillate for the separation of substantially pure benzaldehyde to obtain a yield of at least about 75% based upon the cinnamaldehyde.

8. The method of claim 7 wherein cassia oil is employed as a natural source for the cinnamaldehyde employed in the conversion.

* * * * *